US008522618B1

(12) United States Patent
Ratner

(10) Patent No.: US 8,522,618 B1
(45) Date of Patent: Sep. 3, 2013

(54) DISPOSABLE MANOMETER FOR USE WITH MAGNETIC RESONANCE IMAGING

(75) Inventor: Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 204 days.

(21) Appl. No.: 13/269,638

(22) Filed: Oct. 10, 2011

(51) Int. Cl.
*G01L 7/00* (2006.01)
*A61B 5/02* (2006.01)

(52) U.S. Cl.
USPC .............................. 73/700; 600/487; 600/532

(58) Field of Classification Search
None
See application file for complete search history.

(56) References Cited

U.S. PATENT DOCUMENTS

| | | | |
|---|---|---|---|
| 2,271,268 A | 1/1942 | Longstreet | |
| 3,890,962 A * | 6/1975 | Ramsey, III | 600/486 |
| 3,975,959 A | 8/1976 | Larkin | |
| 4,020,784 A | 5/1977 | Greene | |
| 4,036,216 A * | 7/1977 | Ramsey, III | 600/488 |
| 4,347,744 A | 9/1982 | Buchanan | |
| 4,433,579 A | 2/1984 | Horn | |
| 4,821,713 A | 4/1989 | Bauman | |
| 5,140,982 A | 8/1992 | Bauman | |
| 5,357,951 A | 10/1994 | Ratner | |
| 5,557,049 A * | 9/1996 | Ratner | 73/715 |
| 6,709,403 B1 * | 3/2004 | Ratner | 600/532 |
| 2004/0144179 A1 * | 7/2004 | Ratner | 73/715 |
| 2006/0156823 A1 * | 7/2006 | Lau et al. | 73/716 |
| 2008/0004541 A1 * | 1/2008 | Grane et al. | 600/532 |
| 2011/0088696 A1 * | 4/2011 | Ratner | 128/205.24 |

* cited by examiner

*Primary Examiner* — Andre Allen
(74) *Attorney, Agent, or Firm* — Larson & Larson, P.A.; Frank Liebenow; Justin P. Miller

(57) ABSTRACT

A disposable manometer includes a chamber connectable to a source of respiratory gases via a patient breathing valve and a passageway. A pointer is rotatably disposed with respect to a dial to indicate pressure within the chamber. The pointer has an actuator stem with a spiral-shaped protrusion coupled to a groove within an opening of a stem coupling attached at the center of a diaphragm forming one wall of the chamber. Responsive to pressure entering the chamber, the diaphragm reciprocates against the force of a biasing non-magnetic resilient member moving the stem coupling with respect to the actuator stem of the pointer so that the interaction between the spiral-shaped protrusion and the groove causes rotation of the pointer to indicate the pressure within the chamber. The disposable manometer is useful with any source of respiratory gasses and in the vicinity of any strong magnetic field.

17 Claims, 4 Drawing Sheets

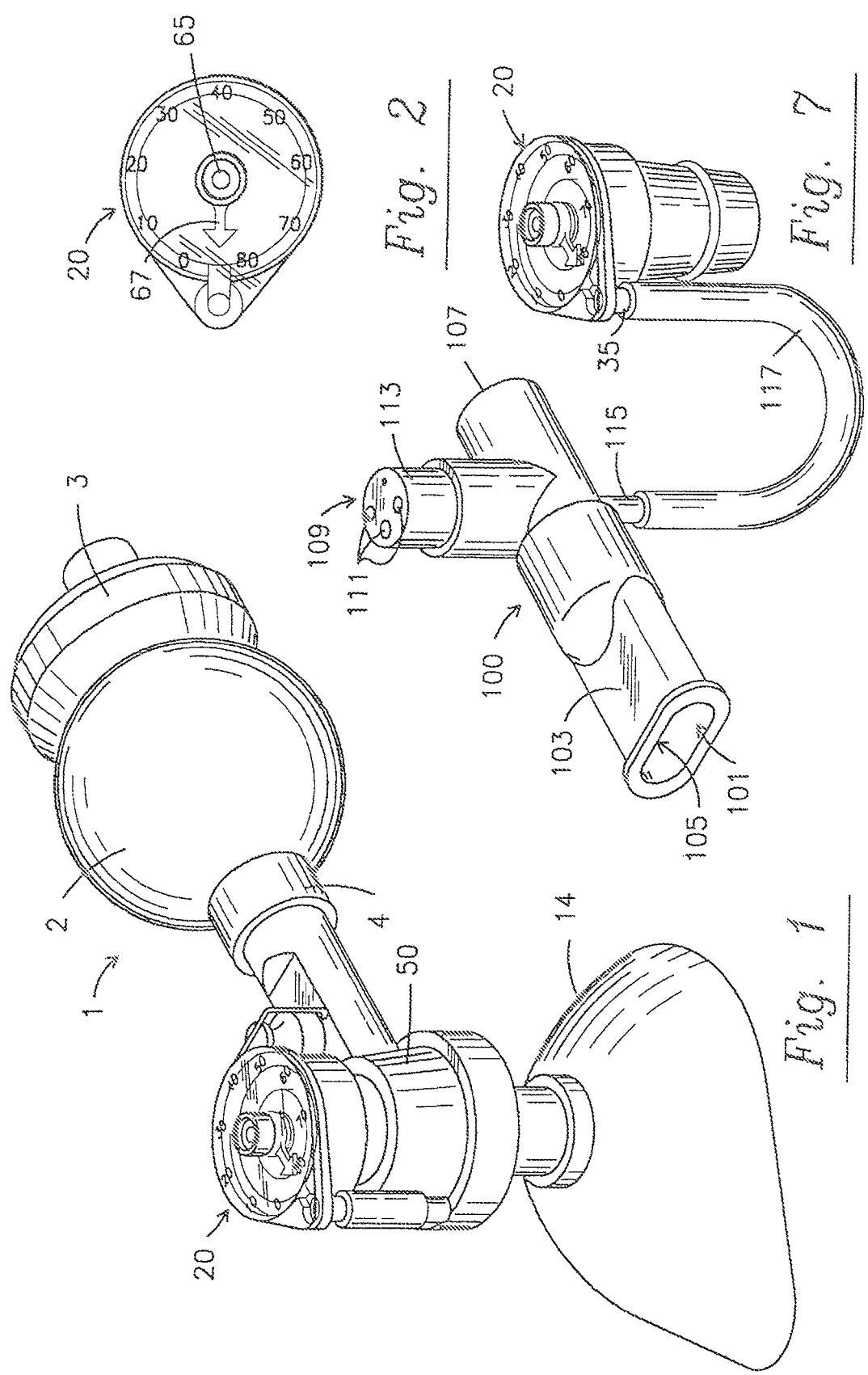

DISPOSABLE MANOMETER FOR USE WITH MAGNETIC RESONANCE IMAGING

FIELD

This invention relates to the field of medicine and more particularly to a device for measuring air pressure that is useful in the vicinity of strong magnetic fields as experienced near an operating Magnetic Resonance Imaging (MRI) system.

BACKGROUND

The present invention relates to a disposable manometer for use with a source of respiratory gases such as a cardio-pulmonary resuscitator (CPR) bag or other ventilation devices. In the prior art, manometers are known, however, such devices do not include all of the features and aspects of the present invention. For example, U.S. Pat. No. 3,975,959 to Larkin which discloses a pressure gauge including a dial with an indicator pointer connected to a cylindrical follower having projections coupled with grooves formed in a stem portion connected to a movable wall. The movable wall is exposed to a source of air pressure and reciprocates the stem portion directly responsive to changes in air pressure to cause rotation of the follower and the pointer. Devices of the prior art will not provide accurate readings when exposed to the strong electromagnetic radiation of various clinical devices such as a Magnetic Resonance Imaging (MRI) system.

Another example is shown in U.S. Pat. No. 5,557,049 to Jeffrey B. Ratner which discloses a disposable manometer. The disclosed manometer has a typical metal spring that operates correctly in most situations but the use of such a manometer in the vicinity of an operational Magnetic Resonance Imaging (MRI) system often results in either a false pressure reading due to the extreme magnetic fields produced by the Magnetic Resonance Imaging system or, in extreme cases, such a manometer is often moved, possibly quickly, creating the possibility of inflicting injuries or damaging equipment.

Applicant is not aware of any helix-style manometer device that, prior to this invention, provides accurate readings in the presence of magnetic fields of devices such as a Magnetic Resonance Imaging (MRI) system.

What is needed is a helix style manometer device that will provide accurate readings in the presence of magnetic fields of a Magnetic Resonance Imaging (MRI) system.

SUMMARY

This application relates to a disposable manometer for use with a source of respiratory gases such as a cardio-pulmonary resuscitator (CPR) bag or other ventilation devices. The disposable manometer includes the following interrelated objects, aspects and features:

The disposable manometer is intended for use in conjunction with a source of respiratory gases such as a cardio-pulmonary resuscitation bag and performs in the presence of magnetic fields encountered in or near devices such as a Magnetic Resonance Imaging (MRI) system. As an example of respiratory gases, the CPR bag includes a bulb squeezable to dispense air through a duckbill check valve to an outlet coupled to a face mask placeable over the patient's nose and mouth. When the patient exhales, the exhaled air is prevented from flowing in the reverse direction by a duckbill check valve and instead lifts the peripheral edges of the duckbill check valve to expose an exhaust port exhausting the air to atmosphere.

The disposable manometer is coupled to air expelled by the source of respiratory gases such as the CPR bag. The operator of the source of respiratory gases (CPR bag) monitors the pressure of gases being supplied to and from the patient.

The disposable manometer includes a housing having a first chamber and a second chamber separated by a movable wall, for example, a diaphragm. The first chamber is connected to the source of air pressure (e.g. the CPR bulb) and the second chamber is exhausted to atmosphere by a suitable vent. A non-ferromagnetic resilient member contained within the second chamber biases the diaphragm.

A stem coupling is attached at approximately the center of the diaphragm and has an opening there through including a generally circular portion and a groove extending radially outwardly from the circular portion. In the preferred embodiment, the stem coupling is elongated into the second chamber and has a surface that engages the non-ferromagnetic resilient member.

A circular dial is provided with indicia thereon indicating a range of pressures. A pointer is rotatably disposed with respect to the dial and includes an actuator stem received within the generally circular portion of the opening through the stem coupling. The actuator stem also has a peripheral outwardly extending spiral-shaped protrusion received within the stem coupling groove. In this way, reciprocations of the stem coupling translate to rotations of the actuator stem as the stem coupling moves upwardly and downwardly acting upon the captured spiral-shaped protrusion of the actuator stem. The non-ferromagnetic resilient member is so sized and configured that when the pressure within the first chamber of the manometer housing is at atmospheric pressure, the pointer is at a rest position. As pressure increases within the first chamber causing the diaphragm and the stem coupling to move downwardly, the pointer moves along the indicia reading the pressure in the first chamber. When the pressure is released, the non-ferromagnetic resilient member restores the position of the diaphragm and stem coupling and thus the position of the pointer to the rest position (e.g. zero).

These and other objects, aspects and features of the disposable manometer will be better understood from the following detailed description of the preferred embodiment when read in conjunction with the appended drawing figures.

BRIEF DESCRIPTION OF THE DRAWINGS

The invention can be best understood by those having ordinary skill in the art by reference to the following detailed description when considered in conjunction with the accompanying drawings in which:

FIG. 1 shows a perspective view of a CPR bag having the inventive disposable manometer attached thereto.

FIG. 2 shows a top view of the disposable manometer.

FIG. 7 shows a perspective view of the inventive disposable manometer fluidly coupled to a patient breathing tube.

DETAILED DESCRIPTION

Figure 3:
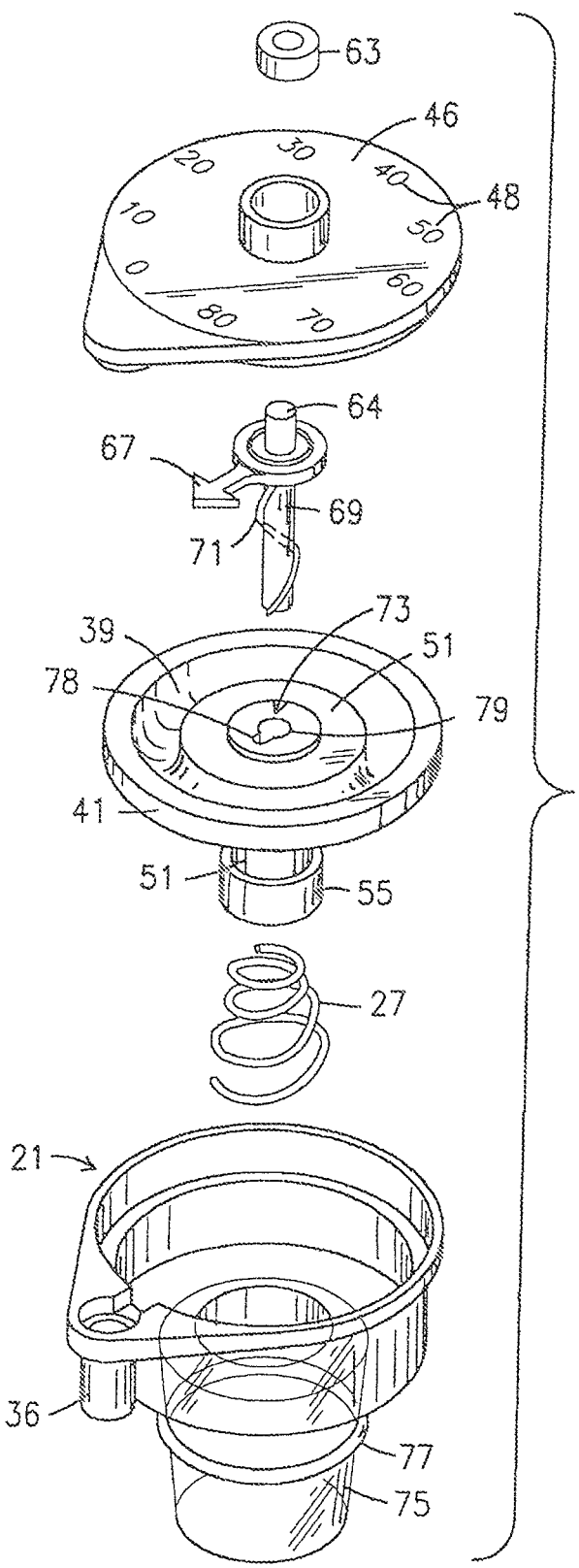
FIG. 3 shows an exploded perspective view of the disposable manometer.

Reference will now be made in detail to the presently preferred embodiments of the invention, examples of which are illustrated in the accompanying drawings. Throughout the following detailed description, the same reference numerals refer to the same elements in all figures.

With reference, first, to FIG. 1, a typical source of respiratory gases such as a cardio-pulmonary resuscitator (CPR) bag or other ventilation devices is generally designated by the reference numeral 1 and, for example, is shown as a squeeze bulb 2 connected between an inlet 3 and an outlet 4. As is known to those skilled in the art, the inlet 3 customarily includes a flexible inlet check valve (not shown) allowing the bulb 2 to fill with air when it is released from a compressed position. The check valve 8 (See FIGS. 5, 6 and 6B) allows a flow of air from the bulb 2 but not into the bulb 2 from the patient. Thus, when the bulb 2 is squeezed, the inlet check valve within the inlet 2 closes and the outlet check valve 8 opens to allow air to flow there past. When the bulb 2 is released, the outlet check valve 8 closes and the inlet check valve within the inlet 3 opens allowing the bulb to be filled with a fresh supply of air. This operation is known to those skilled in the art. Any source of respiratory gases is anticipated.

The outlet fitting 4 leads to a patient breathing valve 50 through passageway 5 (FIGS. 5 and 6) leading to an internal chamber 6 having an outlet 7 controlled by a duckbill-type check valve 8. The check valve 8 has an outlet orifice 9 opened when pressure above a threshold level is within the chamber 6. When pressure in the outlet 7 is greater than pressure in the chamber 6, the opening 9 of the duckbill check valve 8 is closed as shown in FIG. 6B to prevent reverse flow into chamber 6. When reverse flow occurs, with reference to FIG. 6B, the duckbill check valve 8 has a surface 10 resting on a seat 11 forming a portion of the outlet 7. In response to reverse flow of air into the outlet 7, the portion 10 of the duckbill check valve lifts off the seat 11 while the opening 9 of the duckbill check valve 8 remains closed thereby exposing return air flow to the chamber 12 connected to atmosphere via a series of vent ports 13. Thus, the duckbill check valve 8 actually operates as a supply and exhaust valve, supplying the patient by the outlet 7 and the mask 14 (see FIG. 1) and exhausting the exhalations of the patient via the mask 14, outlet 7, chamber 12 and vent ports 13.

The disposable manometer is generally designated by the reference numeral 20 and, with particular reference, first, to FIGS. 5, 6 and 6B, includes a housing 21 defining a first chamber 23 and a second chamber 25 which contains a non-ferromagnetic resilient member 27 for a purpose to be described in greater detail hereinafter. The non-ferromagnetic resilient member 27 is made of a non-ferromagnetic material so that it is not pulled, deformed or moved by the strong magnetic forces encountered in or near a device such as a Magnetic Resonance Imaging System (MRI). Other equipment such as stethoscopes made with non-ferromagnetic materials are available for use in the vicinity of Magnetic Resonance Imaging Systems, but, to date, the industry lacks a disposable manometer that meets such requirements with the disclosed helix and dial.

An elongated passageway 29 interconnects the first chamber 23 of the disposable manometer housing 21 with the chamber 6 of the CPR bag via an orifice 31. Other arrangements of the orifice 31 and passageway 29 are anticipated performing similar functionality.

The passageway 29 includes a portion 33 incorporated into a patient breathing valve extension 50 of the CPR bag 1, a further passageway 35 incorporated into the disposable manometer housing 21 and an entry orifice 37 connecting the passageway 35 to the chamber 23.

Figure 5:
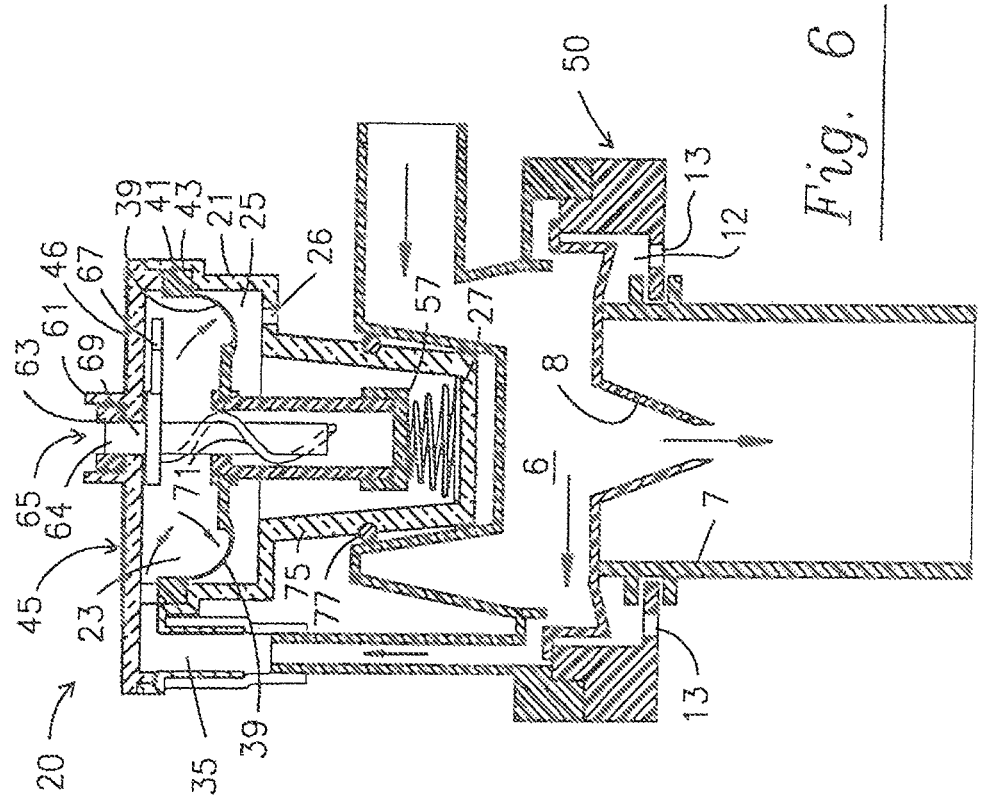
FIG. 5 shows a cross-sectional view through the disposable manometer and a portion of the CPR bag housing with the manometer and diaphragm at an upper position thereof so that the dial pointer reads zero pressure.
Figure 6:
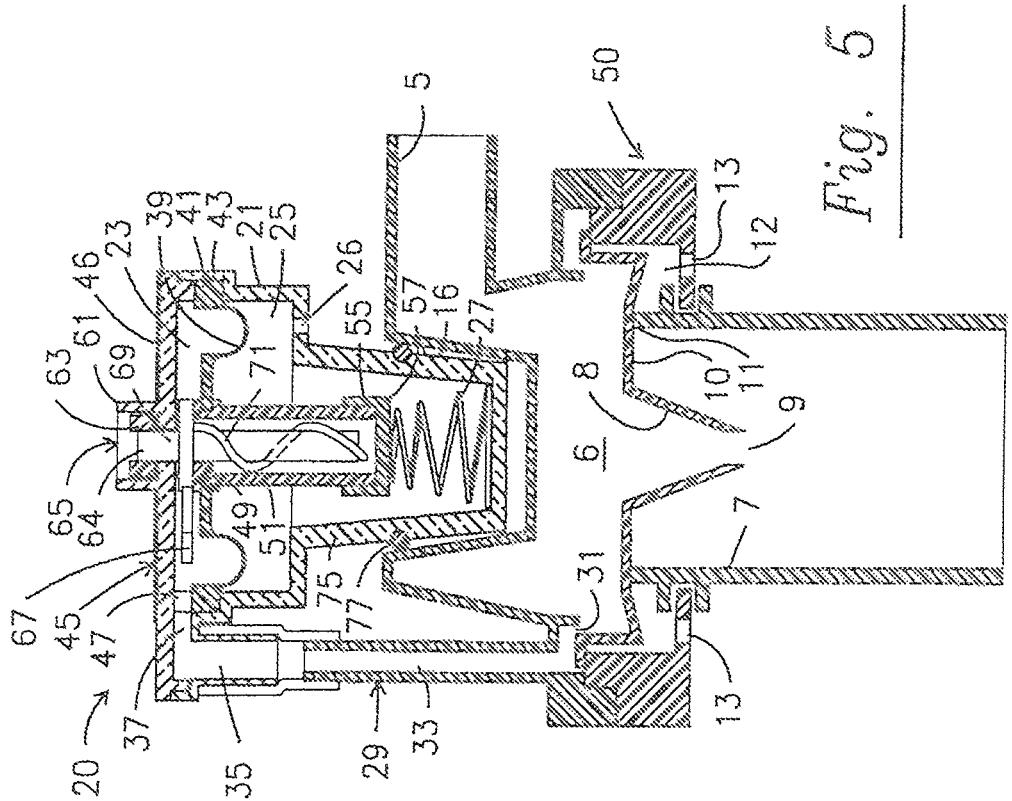
FIG. 6 shows a cross-sectional view through the disposable manometer and a portion of the CPR bag housing showing the effect of air pressure within the first chamber of the manometer housing on the position of the diaphragm and pointer and other associated structure.
Figure 6B:
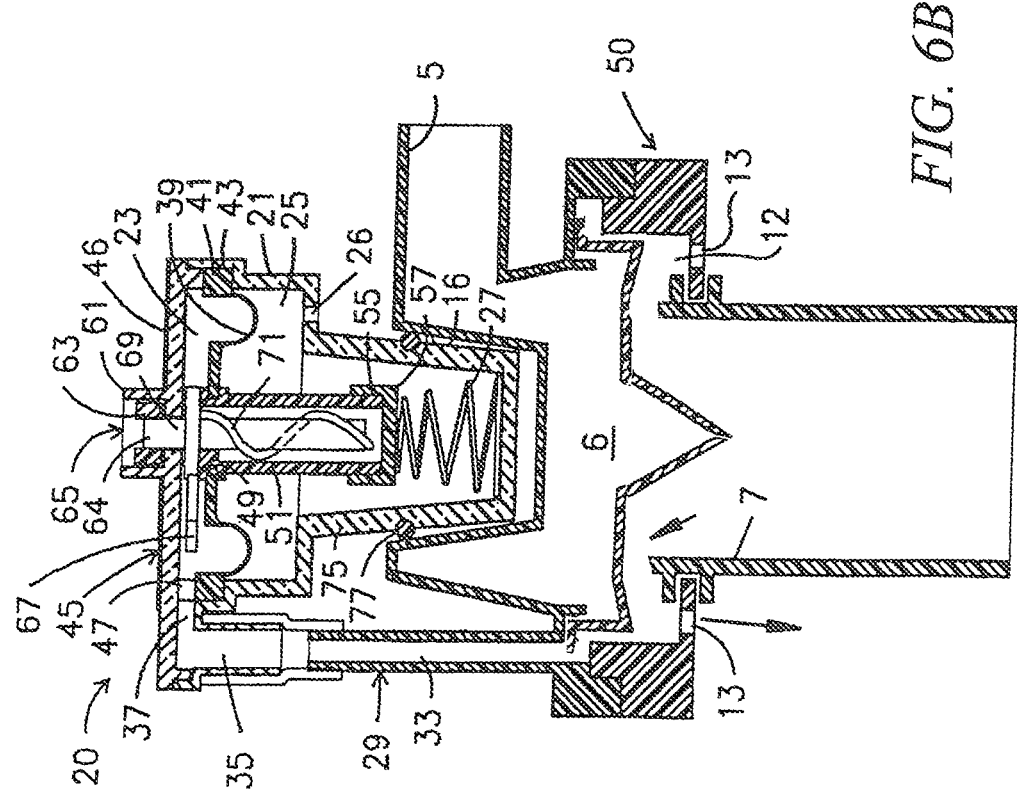
FIG. 6B shows a cross-sectional view through the disposable manometer and a portion of the CPR bag housing showing the effect of air pressure from the patient.

With further reference to FIGS. 5 and 6 in particular, the first chamber 23 and second chamber 25 are separated by a movable wall such as, for example, the diaphragm 39 which includes a peripheral enlarged area 41 captured between a shoulder 43 of the housing 21 and an annular protrusion 47 of a cap 45 of the housing. The diaphragm has a central opening 49 carrying a stem coupling 51 having an internal chamber and a first closure 55 having a surface 57 which rests on the top of the non-ferromagnetic resilient member 27.

The cap 45 overlies the housing 21 and closes the first chamber 23 as best seen in FIGS. 5 and 6. As also seen in these Figures, the cap 45 has an upwardly extending annulus 61 which receives an upper portion of a pointer mechanism 65. A sleeve 63 is interposed between the annulus 61 and an upper protrusion 64 of the pointer mechanism 65 to maintain alignment of the pointer mechanism 65 therein.

Figure 4:
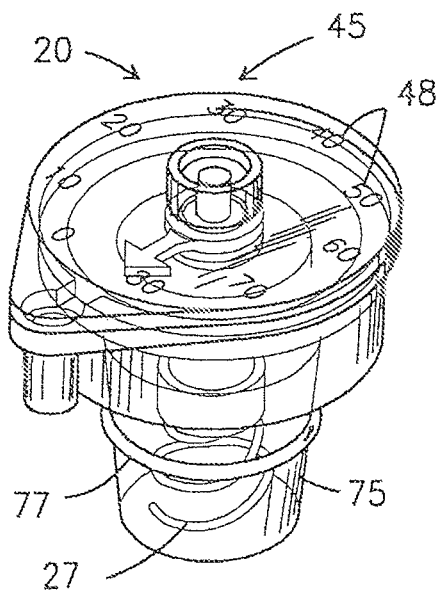
FIG. 4 shows a perspective view of the disposable manometer.

The pointer mechanism 65 includes a pointer 67 attached to an elongated stem 69 having an elongated spiral-shaped protrusion 71 extending there around. As best seen in FIG. 3, the stem coupling 51 has a central opening 73 including a circular portion 79 and a radially outwardly extending groove 78 which receives the protrusion 71 therein while the rest of the stem 69 of the pointer mechanism 65 is slidably received within the circular portion 79 thereof. As should now be understood, when the diaphragm 39 is reciprocated within the chambers 23 and 25, such reciprocations, with the protrusion 71 riding within the groove 78, cause corresponding rotations of the pointer 67. With reference to FIGS. 2, 4 and 5, when the non-ferromagnetic resilient member 27 is in the maximum extended position shown in FIG. 5, the pointer 67 is in the appropriate position to read zero pressure. As air pressure enters the first chamber 23 and causes displacement of the diaphragm 39 downwardly in the view of FIGS. 5 and 6 toward the position shown in FIG. 6, the pointer 67 rotates due to the reciprocation of the stem coupling 51 and the interaction between the groove 78 thereof and the protrusion 71 of the pointer mechanism 65 to cause the pointer 67 to rotate to align with the appropriate indicia indicating the pressure within the chamber 23. As the diaphragm 39 reciprocates either downwardly or upwardly, the pressure within the chamber 25 is always exposed to atmosphere via the vents 26 so that the pressure within the second chamber 25 has no bearing on pressure indications which are indicative of pressure within the CPR bag chamber 6. As shown in FIGS. 3 and 4, the cap 45 has a top surface 46 having indicia 48 indicative of the pressure within the chamber 6 of the CPR bag 1 as indicated by the particular position of the arrow 67. In the preferred embodiment of the present invention, the cap 45 is transparent or translucent with the pointer 67 situated below the cap 45 within the chamber 23 so that the position of the pointer 67 is visible through the cap 45.

All components of the disposable manometer 20 are made from non-ferromagnetic materials including the non-ferromagnetic resilient member 27. The resilient member 27 is non-ferromagnetic so that it is not pulled, deformed or moved by the magnetic forces encountered in or near a Magnetic Resonance Imaging System (MRI). The non-ferromagnetic resilient member 27 is preferably a plastic, brass or phosphor bronze spring, but any non-ferromagnetic resilient member 27 is anticipated including, but not limited to, a gas-filled bladder spring, a gas piston spring or any other known formation of a resilient member that is made of a non-ferromagnetic material so that it is not substantially affected by magnetic forces. It should be noted that some non-ferromagnetic materials are slightly pulled or pushed by magnetic forces, but ferromagnetic materials are a class of materials that are more susceptible to magnetic forces. Examples of ferromagnetic materials are iron and steel. Examples of non-ferromagnetic materials are plastic, bronze, brass and rubber. These examples are not meant to be limiting in any way. Some materials, called Paramagnetic materials, are weakly attracted to a magnet. Examples are platinum and aluminum. Some materials, called Diamagnetic materials, are weakly repelled by both poles. Examples of Diamagnetic materials include carbon, copper, and plastic. Such weekly attracted or weekly repelled materials are generally accepted for use in strong magnetic fields such as in an MRI system, but strongly attracted or repelled materials are not acceptable for use in such systems due to the potential relocation of such devices by the magnetic field and/or potential inaccurate readings from such devices.

As best seen in FIGS. 5 and 6, the patient breathing valve 50 can conveniently include a recess 16 sized to receive a protruding portion 75 of the manometer housing 21 in an interference fit as shown. An O-ring seal 77 may be suitably employed on the protrusion 75 to facilitate the interconnection between the housing 21 and the patient breathing valve 50.

With reference to FIG. 7, a patient breathing tube is generally designated by the reference numeral 100 and includes a mouthpiece 101, an elongated housing 103 having an internal passageway 105, a distal end 107 includes a one-way check valve and an outlet 109 that optionally includes a second one-way check valve and is comprised of orifices 111 formed on a rotatable valve fitting 113 rotatable in a manner well known to those skilled in the art to adjust which of the differing sized orifices 111 fluidly connected to the mouthpiece 101 to thereby facilitate adjustments of the resistance that is provided to the user. A sensing port 115 is provided which interconnects with the passageway 35 of the inventive disposable manometer 20 via a flexible tube 117. The patient breathing tube 100 is a device well known to those skilled in the art and is used to allow a patient to exercise their breathing function by blowing into the mouthpiece 101 and through the variable resistance outlet 109. In this environment of contemplated use, the inventive disposable manometer 20 is employed to display the pressure at which the patient may blow through the breathing tube 100. Of course, the sensing port 115 is directly fluidly connected to the passageway 105 therein.

In the preferred embodiment of the inventive disposable manometer 20, the non-ferromagnetic resilient member 27 is made of a non-ferromagnetic material and the diaphragm 39 is made of a flexible, non-ferromagnetic material such as rubber. The other components thereof are made of non-ferromagnetic materials such as plastic, preferably in an injection molding process. Of course, any other suitable non-ferromagnetic materials are anticipated to be employed for the various components and structures of the inventive manometer 20.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A disposable manometer for sensing and displaying air pressure in a vicinity of a Magnetic Resonance Imaging System, the disposable manometer comprising:
    a) a housing having a first chamber and a second chamber separated by a movable wall, said movable wall carrying a stem coupling having at a first end, a stem coupling opening with an outwardly extending groove and having a distal surface engaging a non-ferromagnetic resilient member within said second chamber;
    b) said first chamber being closed by a cap having pressure indicating indicia thereon, and said cap having a pointer mechanism rotatably mounted thereon and including a pointer alignable with said indicia to indicate pressure in said first chamber, said pointer mechanism including an actuator stem having a spiral-shaped projection thereon, said actuator stem inserted into said stem coupling opening with said spiral-shaped projection engaged within said groove, whereby reciprocations of said stem coupling translate to rotations of said pointer;
    c) said first chamber being fluidly connected to a patient breathing system and said second chamber being vented to atmosphere;
    d) whereby air pressure from the patient breathing system is sensed in said first chamber causing said movable wall to move against force of said non-ferromagnetic resilient member, said pointer thereby rotating into alignment with an indicia representative of pressure in said first chamber.

2. The disposable manometer of claim 1, wherein said movable wall is a diaphragm.

3. The disposable manometer of claim 1, wherein said pointer is located within said first chamber.

4. The disposable manometer of claim 3, wherein said cap is transparent except for said pressure indicating indicia.

5. The disposable manometer of claim 1, wherein said manometer is disposable.

6. The disposable manometer of claim 1, wherein all components of said manometer are made from non-ferromagnetic materials.

7. The disposable manometer of claim 1, wherein the non-ferromagnetic resilient member is made from a non-ferromagnetic material selected from the group consisting of plastic, brass and phosphor bronze.

8. A disposable manometer for sensing and displaying pressure in a patient airway, the disposable manometer comprising:
    a) a housing having an first chamber and a second chamber separated by a movable wall, said movable wall carrying a stem coupling having an opening with an outwardly extending groove at a first end and a surface engaging a non-ferromagnetic resilient member at a distal end and within said second chamber;

b) said first chamber being closed by a cap having pressure indicating indicia thereon, and said cap having a pointer mechanism rotatably mounted thereon and including a pointer alignable with said indicia to indicate pressure in said first chamber, said pointer mechanism including an actuator stem having a spiral-shaped projection thereon, said actuator stem inserted into said stem coupling opening with said spiral-shaped projection engaged within said groove, whereby reciprocations of said stem coupling translate to rotations of said pointer;

c) said first chamber being fluidly connected to a sensing port via a passageway and said second chamber being vented to atmosphere;

d) whereby pressure at said sensing port is sensed in said first chamber causing said movable wall to move against force of said non-ferromagnetic resilient member, said pointer thereby rotating into alignment with an indicia representative of pressure in said first chamber.

9. The disposable manometer according to claim 8, wherein the manometer is disposable.

10. The disposable manometer according to claim 8, wherein the manometer is substantially made from a hardened plastic.

11. The disposable manometer of claim 8, wherein all components of said manometer are made from non-ferromagnetic materials.

12. The disposable manometer of claim 8, wherein the non-ferromagnetic resilient member is made from a non-ferromagnetic material selected from the group consisting of plastic, brass and phosphor bronze.

13. A disposable manometer for sensing and displaying air pressure, the disposable manometer comprising:

a) a housing having an first chamber and a second chamber separated by a movable wall, said movable wall carrying a stem coupling having an opening with an outwardly extending groove at a first end and a surface engaging a non-ferromagnetic resilient member at a distal end and within said second chamber;

b) said first chamber being upwardly closed by a cap having pressure indicating indicia thereon, and said cap having a pointer mechanism rotatably mounted thereon and including a pointer alignable with said indicia to indicate pressure in said first chamber, said pointer mechanism including an actuator stem having a spiral-shaped projection thereon, said actuator stem inserted into said stem coupling opening with said spiral-shaped projection engaged within said groove, whereby reciprocations of said stem coupling translate to rotations of said pointer;

c) said first chamber being fluidly connected to a source of air from source of respiratory gasses via a passageway and said second chamber being vented to atmosphere;

d) whereby pressure at a sensing port is sensed in said first chamber causing said movable wall to move against force of said non-ferromagnetic resilient member, said pointer thereby rotating into alignment with an indicia representative of pressure in said first chamber.

14. The manometer according to claim 13 wherein said movable wall is a diaphragm.

15. The manometer according to claim 13 wherein the manometer housing is made substantially of hardened plastic and is disposable.

16. The disposable manometer of claim 13, wherein all components of said manometer are made from non-ferromagnetic materials.

17. The disposable manometer of claim 13, wherein the non-ferromagnetic resilient member is made from a non-ferromagnetic material selected from the group consisting of plastic, brass and phosphor bronze.

* * * * *